United States Patent [19]

Cavazza

[11] Patent Number: 6,090,848
[45] Date of Patent: *Jul. 18, 2000

[54] COMPOSITIONS AND METHODS FOR INCREASING THE CONCENTRATION AND/ OR MOTILITY OF SPERMATOZOA IN HUMANS

[75] Inventor: Claudio Cavazza, Rome, Italy

[73] Assignee: Sigma-Tau Healthscience S.p.A., Pomezia, Italy

[*] Notice: This patent issued on a continued prosecution application filed under 37 CFR 1.53(d), and is subject to the twenty year patent term provisions of 35 U.S.C. 154(a)(2).

[21] Appl. No.: 09/122,897

[22] Filed: Jul. 28, 1998

Related U.S. Application Data

[63] Continuation-in-part of application No. 08/980,821, Dec. 1, 1997, Pat. No. 5,863,940.
[51] Int. Cl.$^7$ .................... A61K 31/205; A61K 31/225
[52] U.S. Cl. ........................................ 514/547; 514/556
[58] Field of Search ......................... 514/547, 556

[56] References Cited

U.S. PATENT DOCUMENTS

| | | | |
|---|---|---|---|
| 5,037,851 | 8/1991 | Cavazza | 514/556 |
| 5,043,355 | 8/1991 | Cavazza | 514/547 |
| 5,145,871 | 9/1992 | Cavazza | 514/544 |
| 5,173,508 | 12/1992 | Cavazza | 514/547 |
| 5,192,805 | 3/1993 | Cavazza | 514/556 |
| 5,227,518 | 7/1993 | Cavazza | 560/253 |
| 5,270,472 | 12/1993 | Taglialatela et al. | 560/251 |
| 5,418,253 | 5/1995 | Cavazza et al. | 514/547 |
| 5,430,065 | 7/1995 | Cavazza | 514/556 |
| 5,432,199 | 7/1995 | Cavazza | 514/728 |
| 5,494,924 | 2/1996 | Cavazza et al. | 514/357 |
| 5,534,549 | 7/1996 | Tinti et al. | 514/551 |
| 5,591,450 | 1/1997 | Cavazza et al. | 424/451 |
| 5,614,556 | 3/1997 | Cavazza et al. | 514/556 |
| 5,627,212 | 5/1997 | Cavazza et al. | 514/547 |
| 5,637,305 | 6/1997 | Cavazza et al. | 424/401 |
| 5,639,767 | 6/1997 | Cavazza et al. | 514/351 |
| 5,747,536 | 5/1998 | Cavazza | 514/556 |
| 5,753,703 | 5/1998 | Cavazza et al. | 514/556 |
| 5,889,055 | 3/1999 | Howard | 514/561 |

OTHER PUBLICATIONS

R. Golan, et al., "Influence of various substrates on the acetylcarnitine:carnitine ratio in motile and immotile human spermatozoa", *Reprod. Fert.* (1986) 78, 287–293.

Sava R. Micic, et al., "Seminal Carnitine and Glucosidase in Oligospermic and Azoospermic Men", *Journal of Andrology*, vol. 15, Supplement 1994, p. 77S.

Koji Ashizawa, et al., "Inhibition of Flagellar Motility of Fowl Spermatzoa by L–Carnitine: Its Relationship with respiations and Phosphorylation of Axonemal Proteins", *Molecular Reproduction and Development*, 38:318–325 (1994).

C. Jeulin, et al., "Uptake and release of free L–carnitine by boar epididymal spermatozoa in vitro and subsequent acetylation rate", *Journal of Reproduction and Fertility*, (1994), 100:263–271.

R. Deana, et al., "Effect of L–carnitine and L–Aminocarnitine on Calcium Transport, Motility, and Enzyme Release from Ejaculated Bovine Spermatozoa", *Biology of Reproduction*, 41:949–955 (1989).

A. Lee Carter, et al., "A factor in human seminal plasma which affects carnitine accumulation in bovine epididymal sperm", *Fertility and Sterility*, vol. 49, No. 5, May, 1988.

Claudette Jeulin, et al., "Acétylcarnitine et spermatozoïdes: relation avec la maturation épididymaire et la mobilité chez le verrat et l'homme", *Reprod. Nutr. Dévelop.*, 1988, 28(5):1317–1328.

M. Bartellini., et al., "L–carnitine and acetylcarnitine in human sperm with normal and reduced motility", *Europaea Fertilitatis*, vol. 18, No. 1, 1987, pp. 29–31.

D.P. Shalev, "Investigations on the Motility of Human Spermatozoa in a Defined Medium in the Presence of Metabolic Inhibitors and of Carnitine", *Andrologia* 18(4):368–375 (1986).

G. Abbaticchio, et al., "Free L–carnitine in human semen", *Archives of Andrology* 15:137–142 (1985).

G.F. Menhini–Fabris, et al., "Evaluation of Human Seminal Carnitine Content in the Pathophysiology of Reproduction", *3d International Forum of Andrology*, Paris, France, Jun. 18–19, 1985.

G. Fabrizio Menhini–Fabris, et al., "Free L–carnitine in human semen: its variability in different andrologic pathologies", *Fertility and Sterility*, vol. 42, No. 2, pp. 263–267, Aug., 1984.

David A. I. Suter, et al., "The concentrations of free L–carnitine and L–O–Acetylcarnitine in spermatozoa and seminal plasma of normal, fresh, and frozen human semen", *Fertility and Sterility*, vol. 31, No. 5, Mar., 1979, pp. 541–544.

S. Kohengkul, et al., "Levels of L–carnitine and L–O–Acetylcarnitine in normal and infertile human semen: a lower level of L–O–Acetylcarnitine in infertile semen", *Fertility and Sterility*, vol. 28, No. 12, Dec., 1977, pp. 1333–1336.

R. Amendola, et al., "Effects of L–acetylcarnitine (LAC) on the Post–Injury Recovery of Mouse Spermatogenesis monitored by Flow Cytomertyr 1. Recovery after X–Irradiation", *Andrologia* 21, (6):568–575 (1989).

G. Vitali, et al., "Carnitine Supplementation in Human Idiopathic Asthenospermia: Clinical Results", *Drugs Exptl. Clin. Res.* XXI(4) 157–159 (1995).

S. Micic, et al., "Does L–carnitine administered in vivo improve sperm motility?", *ARTA* 1995, vol. 7, pp. 127–130.

M. Costa, et al., "L–carnitine in idiopathic asthenozoospermia: a multicenter study", *Andrologia* 26, 155–159, 1994.

"Diagnostica Andrologica e Fisiopatologia della Riproduzione" 1995, Colle di Mezzo srl—Tutti i Diritti sono Riservati.

"Federation Proceedings—Abstracts" 57$^{th}$ Annual Meeting, Atlantic City, New Jersey, Apr. 15–20, 1973; p. 528.

*Primary Examiner*—Theodore J. Criares
*Attorney, Agent, or Firm*—Oblon, Spivak, McClelland, Maier & Neustadt, P.C.

[57] ABSTRACT

A method is disclosed for treating idiopathic asthenozoospermia and improving sperm quality which comprises orally or parenterally administering to a subject in need thereof a combination preparation comprising either an admixture of or separately packaged L-carnitine and acetyl L-carnitine, or a pharmacologically acceptable salt thereof, in molar ratios ranging from about 4.0:1 to 1:1.5.

34 Claims, No Drawings

COMPOSITIONS AND METHODS FOR INCREASING THE CONCENTRATION AND/OR MOTILITY OF SPERMATOZOA IN HUMANS

This application is a Continuation-in-part (CIP) of application Ser. No. 08/980,821 filed on Dec. 1, 1997, now U.S. Pat. No. 5,863,940.

BACKGROUND OF THE INVENTION

1. Field of the Invention

The present invention relates to compositions and methods for increasing the concentration and/or motility of spermatozoa in humans, including compositions and methods for treating humans affected by idiopathic asthenozoospermia.

2. Description of the Prior Art

Spermatozoa are produced in the testis and undergo post-gonadal modifications in the epididymis to acquire fertilizing ability. In epididymal plasma, high-molecular-weight proteins and such small molecules as free carnitine convert the gametes into "competent" and functional cells. Free L-carnitine is taken up from blood plasma and concentrated in the epididymal lumen. This epididymal secretion is beneficial for spermatozoa and is not merely an excretory waste. Free carnitine goes through the sperm plasma membrane by passive diffusion. Free L-carnitine is acetylated in mature spermatozoa only. The excess acetyl-CoA from the mitochondria is probably stored as acetyl-L-carnitine and modulates the reserves of free CoA essential to the function of the tricarboxylic acid cycle. This property of L-carnitine of buffering CoA in the mitochondrial matrix is known in somatic cells but is accentuated in male germinal cells. The relationship between the endogenous pool of free and acetylated L-carnitine and the percentage of progressive sperm motility indicates a more important metabolic function related to flagellar movement. Thus, the potential of initiating sperm motility which takes place in the epididymis is probably independent of the carnitine system while the energy properties of acetyl-L-carnitine is relevant in situations of "energy crisis". The uptake of cytoplasmic free L-carnitine in mature spermatozoa must be a protective form of mitochondrial metabolism useful to the survival of this isolated cell.

Idiopathic asthenozoospermia, a disorder of sperm motility, is illustrative of certain conditions in this area. It is a post-testicular cause of infertility due to various ethiology, i.e. congenital defects of the sperm tail, maturation defects, immunological disorders or infection. Several drugs for treating idiopathic asthenozoospermia, none of them completely satisfactory, are known.

Antiestrogen drugs (such as clomiphene citrate and tamoxifen) block sex hormones from inhibiting the Follicle Stimulating Hormone (FSH) and the Luteinizing Hormone (LH) in the brain. This triggers an increased release of LH and FSH, which in turn stimulates testosterone production. Increased testosterone level improves spermatogenesis, thus improving sperm density and motility. However a recent randomized, double-blind, multicenter study of 190 couples by the World Health Organization (WHO) showed no effect of clomiphene citrate. Tamoxifen was claimed to improve sperm concentration but no change in motility was usually detected. As for clomiphene, recent studies did not confirm its efficacy.

Testosterone Rebound therapy involves large doses of testosterone that suppress the activity of the patient's pituitary gland. This, in turn, reduces the intratesticular level of testosterone to systemic levels from the usual level. Then the androgen therapy is discontinued in the hope that the system will rebound and improved spermatogenesis will result.

This therapy is not recommended since a large number of treated patients continue to exhibit azoospermia after treatment.

Testolactone, an aromatase inhibitor, prevents the conversion of testosterone to estradiol. It has been tested in patients with idiopathic oligospermia but contrasting results have raised many doubts on its efficacy.

Mesterolone is a synthetic androgen widely used to treat idiopathic male infertility. A recent study sponsored by WHO failed to show any efficacy of this drug.

Human Chorionic Gonadotropin (HCG) is administered empirically to patients with defects in sperm count or motility to correct a presumed intratesticular deficiency of testosterone. Some patients actually experienced a depression of sperm count due to an increased estrogen production by the testes.

Human Menopausal Gonadotropin (HMO) has approximatively equal LH and FSH activity but its use has produced increased sperm counts in only about 50% of cases.

FSH and HCG or HCG and HMG combination therapy does not appear to improve these results any better.

Gonadotropin Releasing Hormone (GnRH) is expensive and disappointing results have been obtained.

Kallikrein can improve sperm motility with increases in sperm concentration but only in about 50% of cases.

Also L-carnitine and acetyl L-carnitine have been studied as candidate drugs for the treatment of asthenospermia.

Vitali G. et al. (Drugs Exptl. Clin. Res. XXI(4):157–159, 1995) investigated the effectiveness of L-carnitine administration in a group of patients with idiopathic asthenospermia. A favourable effect of the compound on sperm motility and rapid linear progression has been shown in 37 out of 47 patients treated. Same results were obtained by Török L. (Dermatol. Monatsschr. 169:572–575, 1983).

Costa M. et al. (Andrologia, 26: 155–159, 1994) showed a significant improvement, both in a quantitative and qualitative manner, in spermatozoa! motility after administration of L-carnitine. They speculated that in infertile patients impairment occurred either in epididymal function or in the ability of sperm to capture and utilize carnitine (Bartelloni M. et al., Acta Eur. Fertil. 18:29–31, 1987). Thus, the administration of carnitine would provide additive substrate for sperm energy metabolism and motility.

Müller-Tyl E. et al. (Fertilität 4:1–4, 1988) suggested that L-carnitine therapy can be successful in infertile patients. In fact, results demonstrated a continuous increase in the carnitine levels in sperm following carnitine treatment and a contemporary increase in motility and sperm cell count.

Loumbakis P. et al. (XIIth Congress of the European Association of Urology. Paris, Sep. 1–4, 1996) provided preliminary data suggesting that carnitine administration may positively affect sperm quality.

Finally, Moncada M. L. et al. (Acta Eur. Fertil. 23(5): 221–224, 1992) investigated the effect on sperm quality of acetyl-L-carnitine administered to patients affected by idiopathic oligoasthenospermia. Acetyl-L-carnitine had no effects on sperm density, but showed to increase progressive sperm motility.

SUMMARY OF THE INVENTION

Accordingly, it is an object of the invention to provide various compositions and methods for increasing the concentration of spermatozoa in humans.

It is another object of the invention to provide various compositions and methods for increasing the motility of spermatozoa in humans.

It is another object of the invention to provide various compositions and methods for treating humans suffering from idiopathic asthenozoospermia.

The above objects and others which are apparent from the description of the invention below relate to the discovery that administration of both L-carnitine and acetyl L-carnitine, or a pharmacologically acceptable salts[1] thereof, to a human is effective for increasing the concentration and/or motility of spermatozoa in humans, including treating idiopathic asthenozoospermia, even in individuals not responding to known, conventional aforesaid treatments.

[1] The term "pharmacologically acceptable salts" is used herein simply to refer to those salts which are safe for use in food stuffs or in prescription products. The term is not used to indicate or suggest a product requiring a prescription.

It has been found that the compositions and methods of the present invention exhibit a marked superiority in increasing the concentration of spermatozoa and/or the motility of spermatozoa in humans, including treating humans suffering from idiopathic asthenozoospermia, over the results obtained by administering L-carnitine or acetyl L-carnitine individually, i.e. as monotherapies.

DESCRIPTION OF SPECIFIC EMBODIMENTS

The L-carnitine and acetyl L-carnitine can be in any form suitable for oral or parenteral administration to a human. The L-carnitine and acetyl L-carnitine can be formulated together, as an admixture, or they can be formulated separately (packaged separately), using known techniques. The L-carnitine and acetyl L-carnitine can be administered in such a manner to an individual either as the admixture or separately formulated.

Depending on various factors, such as concentration of active ingredient(s), the L-carnitine and acetyl L-carnitine according to the invention may be sold as food supplements, nutritional supplements, or as therapeutic products including over-the-counter and prescription products.

Various molar ratios of L-carnitine to acetyl L-carnitine, or the pharmacologically acceptable salts thereof, may be used in accordance with the invention, including molar ratios ranging from 4.0:1 to 1:1.5. Preferred ratios include molar ratios ranging from about 3.2:1 to 2.8:1 and molar ratios corresponding to about 1:1.

The combination preparations of the present invention, when in unit dosage form, comprise from 2.5 g to 0.22 g of L-carnitine inner salt and from 0.28 g to 1.3 g of acetyl L-carnitine or equimolar amounts of the pharmacologically acceptable salts thereof.

Preferred combination preparations in unit dosage form comprise 1.0 g of L-carnitine inner salt and 0.5 g of acetyl L-carnitine inner salt or equimolar amounts of the pharmacologically acceptable salts thereof.

It was, furthermore, found that although the daily dose of the aforesaid active ingredients to be administered is determined from the age, weight and condition of the patient, utilizing sound professional judgement, it is generally advisable to administer in a single dose or multiple dose administration regimen about 0.8 to 2.5 g/day of L-carnitine and about 1.0 to 1.5 g/day of acetyl L-carnitine or equivalent molar amounts of the pharmacologically acceptable salts thereof. Larger doses can be safely administered in view of the extremely low toxicity of the aforesaid active ingredients.

A clinical study aimed at evaluating whether supplementation with the drug association therapy is effective in improving reduced sperm motility over L-carnitine monotherapy and acetyl L-carnitine monotherapy, respectively, is hereinbelow described.

Thirty-six patients responding to the following inclusion/ exclusion criteria were enrolled.

"Inclusion criteria": young, infertile males with idiopathic asthenozoospermia recognized as the sole cause of infertility at least two years duration; semen parameters to be met on at least two samples: sperm concentration (M/ml) between 10–20, motility (%) >20 <40 at 2 hours, rapid linear progression (%) <20 at 2 hours.

Exclusion criteria: undescended testes, varicocele (grade 3), traumatic or infection related testicular atrophy, obstruction, inflammation and infection of the genital tract, any endocrine disorder affecting the hypothalamic-pituitary-gonadal axis; post-pubertal mumps, evidence of antisperm antibodies.

All patients gave their informed consent to this open study.

Semen was obtained by masturbation after at least four days of sexual abstinence. The samples were analysed within one hour after ejaculation for all the parameters by the standard methods recommended by the WHO (1987). The sperm motility was studied using a computer motility analyser on at least two specimens.

Semen analysis and motility assessment were carried out at baseline and after 4 months of L-carnitine (N=12) or acetyl-L-carnitine (N=12) or association drug (N=12) treatment.

L-carnitine was administered at the dose of 2 g/day (2×500 mg tablet b.i.d., after meals) for 4 months. Acetyl-L-carnitine was administered at the dose of 4 g/day (2×1 g sachet b.i.d., after meals) for 4 months. The association drug treatment (L-carnitine+acetyl-L-carnitine) was administered at the dose of 2 g/day (2×500 mg tablet composed of 220 mg L-carnitine and 280 mg acetyl-L-carnitine, b.i.d. after meals) for 4 months.

Data were analyzed using Student's "t" test for paired data.

Results
Semen analysis

| Variable (mean ± SD) | Baseline | L-Carnitine | Baseline | Acetyl-L-carnitine | Baseline | LC + ALC |
|---|---|---|---|---|---|---|
| Motility (%) | 26.8 ± 5.4 * | 33.1 ± 4.6 | 24.9 ± 4.5 # | 30.9 ± 4.5 | 26.3 ± 4.5 § | 40.8 ± 6.3 a b |
| Concentration (M/ml) | 15.7 ± 2.0 ** | 26.0 ± 2.8 b | 16.7 ± 3.6 | 18.1 ± 2.0 | 16.2 ± 2.4 § | 30.8 ± 3.6 a b |
| Spermatozoa with rapid linear progression (%) | 9.8 ± 1.5 ** | 17.0 ± 1.5 | 10.3 ± 1.1 b | 16.0 ± 1.2 | 10.0 ± 1.2 § | 21.6 ± 2.8 ** b |

LC + ALC = L-Carnitine + Acetyl-L-carnitine
* $p \leq 0.05$ versus L-Carnitine
$p \leq 0.05$ versus Acetyl-L-carnitine
§ $p \leq 0.001$ versus L-Carnitine + Acetyl-L-carnitine
a $p \leq 0.01$ versus L-Carnitine
b $p \leq 0.001$ versus Acetyl-L-carnitine
** $p \leq$ Cool versus L-Carnitine Before treatment values of seminal parameters were below those of WHO normal ranges.

The association drug treatment significantly increased the concentration and the motility of spermatozoa as well as the percentage of spermatozoa with rapid linear progression in comparison to L-carnitine and acetyl-L-carnitine monotherapy treatments.

The medicament of the present invention can be prepared by mixing—either together or separately packaged—the active ingredients (L-carnitine inner salt and acetyl L-carnitine inner salt or a pharmacologically acceptable salt thereof) with excipients suitable for the formulation of compositions which lend themselves to enteral administration (particularly oral administration) or to parenteral administration (particularly by the intramuscular or intravenous route). All such excipients shall be readily apparent to one having ordinary skill in this art.

Pharmaceutically acceptable salts of the aforesaid active ingredients include all pharmaceutically acceptable salts which are prepared by the addition of an acid to L-carnitine and acetyl L-carnitine inner salts and which do not give rise to undesired toxic or side effects. The formation of pharmaceutically acceptable acid addition salts is well known in pharmaceutical technology.

Non-limiting examples of suitable salts include chloride; bromide; iodide; aspartate, particularly acid aspartate; citrate, particularly acid citrate; tartrate; phosphate, particularly acid phosphate; fumarate, particularly acid fumarate; glycerophosphate; glucose phosphate; lactate; maleate, particularly acid maleate; orotate; oxalate, particularly acid oxalate; sulphate, particularly acid sulphate; trichloroacetate; trifluoro acetate and methanesulphonate.

A preferred embodiment of the invention uses L-carnitine acid fumarate and acetyl L-carnitine hydrochloride, most preferably in a molar ratio of about 3:1. This and other preferred embodiments may be illustrated by sachets containing the following composition:

|  | | Composition 1 | | Composition 2 | | Composition 3 | | Composition 4 |
|---|---|---|---|---|---|---|---|---|
| Acetyl-L-carnitine, HCl | g | 0.500 | g | 1.000 | g | 1.000 | g | 1.500 |
| equivalent to | | | | | | | | |
| Acetyl-L-carnitine inner salt | g | 0.424 (2.1 mMoles) | g | 0.848 (4.2 mMoles) | g | 0.848 (4.2 mMoles) | g | 1.272 (6.2 mMoles) |
| L-carnitine fumarate | g | 1.725 | g | 3.450 | g | 4.312 | g | 1.725 |
| equivalent to | | | | | | | | |
| L-carnitine inner salt | g | 1.000 (6.2 mMoles) | g | 2.000 (12.4 mMoles) | g | 2.500 (15.5 mMoles) | g | 1.000 (6.2 mMoles) |
| L-carnitine/acetyl-L-carnitine molar ratio | | ~3 | | ~3 | | ~3.7 | | ~1 |
| Fructose | g | 1.000 | g | 2.000 | g | 2.000 | g | 2.000 |
| Citric acid | g | 0.050 | g | 0.050 | g | 0.050 | g | 0.050 |
| Saccharin sodium | g | 0.008 | g | 0.008 | g | 0.008 | g | 0.008 |
| Tonic water flavor | g | 0.050 | g | 0.050 | g | 0.050 | g | 0.050 |
| D-mannitol | g | 0.666 | g | 0.441 | g | 0.579 | g | 1.666 |
| Colloidal silicon dioxide | g | 0.001 | g | 0.001 | g | 0.001 | g | 0.001 |

The contents of one sachet should be mixed with at least 120 mL of water or other beverage.

Two sachets of the lowest dosage composition (i.e., composition 1) should be taken per day, preferably one in the morning and one at night, preferably for at least six months.

This application is a continuation-in-part of application Ser. No. 08/980,821, filed Dec. 1, 1997, pending.

Obviously, numerous modifications and variations of the present invention are possible in light of the above teachings. It is therefore to be understood that within the scope of the appended claims, the invention may be practiced otherwise than as specifically described therein.

What is claimed is:

1. A combination of admixed or separately packaged L-carnitine and acetyl L-carnitine or a pharmacologically acceptable salt thereof, synergistic effective molar ratio of L-carnitine:acetyl L-carnitine of 2.8:1 to 4.0:1, capable of increasing synergistically the concentration or motility of spermatozoa in a human, said combination being in a form suitable for oral or parenteral administration.

2. A combination of L-carnitine and acetyl L-carnitine in a form suitable for oral administration according to claim 1.

3. A combination of L-carnitine and acetyl L-carnitine in a form suitable for parenteral administration according to claim 1.

4. An admixture of L-carnitine and acetyl L-carnitine according to claim 1.

5. Separately packaged L-carnitine and acetyl L-carnitine according to claim 1.

6. The combination of claim 1, comprising a pharmacologically acceptable salt of L-carnitine or acetyl L-carnitine, said salt being selected from the group consisting of chloride, bromide, iodide, aspartate, citrate, tartrate, phosphate, fumarate, glycerophosphate, glucose phosphate, lactate, maleate, orotate, oxalate, sulphate, trichloroacetate, trifluoroacetate and methanesulphonate.

7. The L-carnitine and acetyl L-carnitine of claim 6, wherein said salt is selected from the group consisting of acid aspartate, acid citrate, acid phosphate, acid fumarate, acid maleate, acid oxalate, and acid sulphate.

8. L-carnitine acid fumarate and acetyl L-carnitine hydrochloride according to claim 1.

9. The combination of claim 6, containing pharmacologically aceptable salts of both L-carnitine and acetyl L-carnitine.

10. The admixture of L-carnitine and acetyl L-carnitine of claim 4, in a form suitable for oral administration.

11. The admixture of L-carnitine and acetyl L-carnitine of claim 4, in a form suitable for parenteral administration.

12. The combination of claim 1, comprising L-carnitine and acetyl L-carnitine in a molar ratio of about 3:1.

13. The combination of claim 12, comprising L-carnitine acid fumarate and acetyl L-carnitine hydrochloride.

14. A method for increasing the concentration or motility of spermatozoa in a human in need thereof, comprising administering to said human synergistic effective amounts of L-carnitine and acetyl L-carnitine or a pharmacologically acceptable salt thereof, in an amount and ratio providing said synergistic increase in concentration or motility of spermatozoa.

15. A method for treating idiopathic asthenozoospermia in a human, according to claim 14.

16. The method of claim 14, comprising administering a pharmacologically acceptable salt of L-carnitine or acetyl L-carnitine, said salt being selected from the group consisting of chloride, bromide, iodide, aspartate, citrate, tartrate, phosphate, fumarate, glycerophosphate, glucose phosphate, lactate, maleate, orotate, oxalate, sulphate, trichloroacetate, trifluoroacetate and methanesulphonate.

17. The method of claim 16, comprising administering a salt selected from the group consisting of acid aspartate, acid citrate, acid phosphate, acid fumarate, acid maleate, acid oxalate, and acid sulphate.

18. The method of claim 16, comprising administering L-carnitine acid fumarate and acetyl L-carnitine.

19. The method of claim 14, comprising administering to said human L-carnitine and acetyl L-carnitine in a molar ratio of 4.0:1 to 1:1.5.

20. The method of claim 18, comprising administering L-carnitine acid fumarate and acetyl L-carnitine hydrochloride in a molar ratio of 4.0:1 to 1:1.5.

21. The combination of claim 1, in unit dosage form, comprising from 0.22 to 2.5 g of L-carnitine and from 0.28 to 1.3 g of acetyl L-carnitine or equimolar amounts of the pharmacologically acceptable salts thereof.

22. A combination of admixed or separately packaged L-carnitine and acetyl L-carnitine, or a pharmacologically acceptable salt thereof, capable of increasing the concentration or motility of spermatozoa in a human, said combination being in a form suitable for oral or parental administration and comprising at least one unit dosage of from 0.22 to 2.5 g. of L-carnitine and from 0.28 to 1.3 g of acetyl L-carnitine.

23. A combination of L-carnitine and acetyl L-carnitine in a form suitable for oral administration according to claim 22.

24. A combination of L-carnitine and acetyl L-carnitine in a form suitable for parenteral administration according to claim 22.

25. An admixture of L-carnitine and acetyl L-carnitine according to claim 22.

26. Separately packaged L-carnitine and acetyl L-carnitine according to claim 22.

27. The combination of claim 22, comprising a pharmacologically acceptable salt of L-carnitine or acetyl L-carnitine, said salt being selected from the group consisting of chloride, bromide, iodide, aspartate, citrate, tartrate, phosphate, fumarate, glycerophosphate, glucose phosphate, lactate, maleate, orotate, oxalate, sulphate, trichoroacetate, trifluoroacetate and methanesulphonate.

28. The L-carnitine and acetyl L-carnitine of claim 27, wherein said salt is selected from the group consisting of acid aspartate, acid citrate, acid phosphate, acid fumarate, said maleate, acid oxalate, and acid sulphate.

29. L-carnitine acid fumarate and acetyl L-carnitine hydrocholoride according to claim 22.

30. The combination of claim 27, containing pharmacologically acceptable salts of both L-carnitine and acetyl L-carnitine.

31. The admixture of L-carnitine and acetyl L-carnitine of claim 25, in a form suitable for oral administration.

32. The admixture of L-carnitine and acetyl L-carnitine of claim 25, in a form suitable for parenteral administration.

33. The combination of claim 22, comprising L-carnitine acid fumarate and acetyl L-carnitine in a molar ratio of 2.8:1 to 4.0:1.

34. The combinations of claim 33, comprising L-carnitine acid fumarate and acetyl L-carnitine hydrochloride.

* * * * *